United States Patent
Glover

(10) Patent No.: US 9,150,465 B2
(45) Date of Patent: Oct. 6, 2015

(54) INTEGRATION OF CYCLIC DEHYDROGENATION PROCESS WITH FCC FOR DEHYDROGENATION OF REFINERY PARAFFINS

(75) Inventor: Bryan K. Glover, Algonquin, IL (US)

(73) Assignee: UOP LLC, Des Plaines, IL (US)

(*) Notice: Subject to any disclaimer, the term of this patent is extended or adjusted under 35 U.S.C. 154(b) by 405 days.

(21) Appl. No.: 12/886,966

(22) Filed: Sep. 21, 2010

(65) Prior Publication Data

US 2012/0071701 A1    Mar. 22, 2012

(51) Int. Cl.
| | |
|---|---|
| C07C 4/06 | (2006.01) |
| C07C 2/56 | (2006.01) |
| C07C 5/333 | (2006.01) |
| C07C 6/04 | (2006.01) |
| C10G 11/18 | (2006.01) |
| C10G 57/00 | (2006.01) |
| C10G 70/00 | (2006.01) |

(52) U.S. Cl.
CPC ... *C07C 4/06* (2013.01); *C07C 2/56* (2013.01); *C07C 5/3335* (2013.01); *C07C 5/3337* (2013.01); *C07C 6/04* (2013.01); *C10G 11/18* (2013.01); *C10G 57/00* (2013.01); *C10G 57/005* (2013.01); *C10G 70/00* (2013.01); *C07C 2521/06* (2013.01); *C07C 2523/26* (2013.01); *C07C 2523/42* (2013.01); *C10G 2400/20* (2013.01)

(58) Field of Classification Search
CPC ............ C07C 4/00; C07C 4/02; C07C 4/06; C07C 5/3337; C07C 5/3335; C07C 6/04; C07C 2/56; C07C 2521/06; C07C 2523/26; C07C 2523/42; C10G 70/00; C10G 57/00; C10G 57/005; C10G 11/18; C10G 2400/20
USPC ......... 585/324, 314, 315, 331, 628, 655, 653, 585/659, 648, 649, 650, 651, 654, 660, 661, 585/662; 208/67, 69, 70, 49, 66, 72, 73, 76
See application file for complete search history.

(56) References Cited

U.S. PATENT DOCUMENTS

| | | | |
|---|---|---|---|
| 2,831,041 A * | 4/1958 | Sieg et al. ................. 585/624 |
| 2,889,383 A * | 6/1959 | Green ......................... 585/602 |
| 3,726,789 A * | 4/1973 | Kovach ....................... 208/80 |
| 3,781,376 A * | 12/1973 | Manning ..................... 585/662 |
| 4,851,374 A * | 7/1989 | Yan et al. .................... 502/42 |
| 4,969,987 A * | 11/1990 | Le et al. ...................... 208/67 |
| 5,026,935 A | 6/1991 | Leyshon et al. |
| 5,026,936 A | 6/1991 | Leyshon et al. |
| 5,043,522 A | 8/1991 | Leyshon et al. |
| 5,160,424 A * | 11/1992 | Le et al. ...................... 208/67 |
| 5,191,131 A * | 3/1993 | Takahata et al. ........... 585/324 |
| 5,447,622 A * | 9/1995 | Kerby et al. ................ 208/78 |
| 6,258,257 B1 | 7/2001 | Swan, III et al. |
| 6,288,298 B1 | 9/2001 | Rodriguez et al. |
| 6,300,537 B1 | 10/2001 | Strohmaier et al. |
| 6,307,117 B1 * | 10/2001 | Tsunoda et al. ............ 585/651 |
| 6,362,385 B1 * | 3/2002 | Iezzi et al. .................. 585/661 |
| 6,410,813 B1 * | 6/2002 | Dath et al. .................. 585/653 |
| 6,521,563 B2 | 2/2003 | Strohmaier et al. |
| 6,791,002 B1 | 9/2004 | Abrevaya et al. |
| 6,867,341 B1 | 3/2005 | Abrevaya et al. |
| 2003/0232720 A1 * | 12/2003 | Alerasool et al. .......... 502/317 |
| 2007/0265482 A1 * | 11/2007 | Tsunoda et al. ............ 585/651 |
| 2008/0200745 A1 * | 8/2008 | Sigl et al. ................... 585/643 |
| 2009/0030252 A1 * | 1/2009 | Senetar et al. ............. 585/324 |
| 2009/0112032 A1 | 4/2009 | Eng |

FOREIGN PATENT DOCUMENTS

| | | | |
|---|---|---|---|
| EP | 0109060 B1 | 3/1987 |
| EP | 0109059 B1 | 7/1987 |

OTHER PUBLICATIONS

Abdullah M. Aitani, "Propylene Production," 2006, Taylor & Francis Group, pp. 2461-2465.*

Calvin H. Bartholomew and Robert J. Farrauto. "Hydrogenation and Dehydrogenation of Organic Compounds," 2006, John Wiley & Sons, pp. 533-537.*

Kaiser et al., Better Ethylene Separation Unit, Hydrocarbon Processing, Nov. 1988, pp. 57-61.

* cited by examiner

*Primary Examiner* — In Suk Bullock
*Assistant Examiner* — Philip Louie

(57) ABSTRACT

A process for increasing light olefin yields from the fluidized catalytic cracking process. The process combines small units to treat the paraffinic components in the product streams from the fluidized cracking process. The paraffins are dehydrogenated and light olefins are separated. Heavier olefins are passed to an olefin cracking unit for increasing the yields of ethylene and propylene.

12 Claims, No Drawings

INTEGRATION OF CYCLIC DEHYDROGENATION PROCESS WITH FCC FOR DEHYDROGENATION OF REFINERY PARAFFINS

FIELD OF THE INVENTION

The field of the invention is the production of light olefins. In particular, the field is the production of light olefins using the cracking of heavier hydrocarbons, and the processing of intermediate streams from the cracking process.

BACKGROUND OF THE INVENTION

Ethylene and propylene, light olefin hydrocarbons with two or three atoms per molecule, respectively, are important chemicals for use in the production of other useful materials, such as polyethylene and polypropylene. Polyethylene and polypropylene are two of the most common plastics found in use today and have a wide variety of uses both as a material fabrication and as a material for packaging. Other uses for ethylene and propylene include the production of vinyl chloride, ethylene oxide, ethylbenzene and alcohol. Steam cracking or pyrolysis of hydrocarbons produces most of the ethylene and some propylene. One of the disadvantages of steam cracking is the low ratio of propylene to ethylene. Hydrocarbons used as feedstock for light olefin production include natural gas, petroleum liquids, and carbonaceous materials including coal, recycled plastics or any organic material.

An ethylene plant is a very complex combination of reaction and gas recovery systems. The feedstock is charged to a cracking zone in the presence of steam at effective thermal conditions to produce a pyrolysis reactor effluent gas mixture. The pyrolysis reactor effluent gas mixture is stabilized and separated into purified components through a sequence of cryogenic and conventional fractionation steps. A typical ethylene separation section of an ethylene plant containing both cryogenic and conventional fractionation steps to recover an ethylene product with a purity exceeding 99.5% ethylene is described in an article by V. Kaiser and M. Picciotti, entitled, "Better Ethylene Separation Unit." The article appeared in HYDROCARBON PROCESSING MAGAZINE, November 1988, pages 57-61 and is hereby incorporated by reference.

Methods are known for increasing the conversion of portions of the products of the ethylene production from a zeolitic cracking process to produce more propylene by a disproportionation or metathesis of olefins. Such processes are disclosed in U.S. Pat. No. 5,026,935 and U.S. Pat. No. 5,026,936 wherein a metathesis reaction step is employed in combination with a catalytic cracking step to produce more propylene by the metathesis of $C_2$ and $C_4$ olefins obtained from cracking. The catalytic cracking step employs a zeolitic catalyst to convert a hydrocarbon stream having 4 or more carbon atoms per molecule to produce olefins having fewer carbon atoms per molecule. The hydrocarbon feedstream to the zeolitic catalyst typically contains a mixture of 40 to 100 wt-% paraffins having 4 or more carbon atoms per molecule and 0 to 60 wt-% olefins having 4 or more carbon atoms per molecule. In U.S. Pat. No. 5,043,522, it is disclosed that the preferred catalyst for such a zeolitic cracking process is an acid zeolite, examples includes several of the ZSM-type zeolites or the borosilicates. Of the ZSM-type zeolites, ZSM-5 was preferred. It was disclosed that other zeolites containing materials which could be used in the cracking process to produce ethylene and propylene included zeolite A, zeolite X, zeolite Y, zeolite ZK-5, zeolite ZK-4, synthetic mordenite, dealuminized mordenite, as well as naturally occurring zeolites including chabazite, faujasite, mordenite, and the like. Zeolites which were ion-exchanged to replace alkali metal present in the zeolite were preferred. Preferred alkali exchange cations were hydrogen, ammonium, rare earth metals and mixtures thereof.

European Patent No. 109,059B1 discloses a process for the conversion of a feedstream containing olefins having 4 to 12 carbon atoms per molecule into propylene by contacting the feedstream with a ZSM-5 or a ZSM-11 zeolite having a silica to alumina atomic ratio less than or equal to 300 at a temperature from 400 to 600° C. The ZSM-5 or ZSM-11 zeolite is exchanged with a hydrogen or an ammonium cation. The reference also discloses that, although the conversion to propylene is enhanced by the recycle of any olefins with less than 4 carbon atoms per molecule, paraffins which do not react tend to build up in the recycle stream. The reference provides an additional oligomerization step wherein the olefins having 4 carbon atoms are oligomerized to facilitate the removal of paraffins such as butane and particularly isobutane which are difficult to separate from $C_4$ olefins by conventional fractionation. In a related European Patent No. 109,060B1, a process is disclosed for the conversion of butenes to propylene. The process comprises contacting butenes with a zeolitic compound selected from the group consisting of silicalites, boralites, chromosilicates and those zeolites ZSM-5 and ZSM-11 in which the mole ratio of silica to alumina is greater than or equal to 350. The conversion is carried out at a temperature from 500° C. to 600° C. and at a space velocity of from 5 to 200 kg/hr of butenes per kg of pure zeolitic compound. The European Patent No. 109,060B1 discloses the use of silicalite-1 in an ion-exchanged, impregnated, or co-precipitated form with a modifying element selected from the group consisting of chromium, magnesium, calcium, strontium and barium.

U.S. Pat. No. 6,867,341 to Abrevaya et al. teaches naphtha cracking using a catalyst comprising a molecular sieve having 10-membered rings with channels of length 0.1 to 0.3 micrometers and having a silicon to aluminum atomic ratio of about 20 to about 200. In particular, examples are presented showing that a high Si/Al2 ratio Ferrierite catalyst is more effective for naphtha conversion and gives higher yields of the desired products ethylene and propylene than other zeolites examined. Preferred operating temperatures in the range 650 to 670 C are indicated, and operating pressures should be as low as can be economically achieved.

U.S. Pat. No. 6,288,298 to Rodriguez et al. teaches cracking of a naphtha stream that contains a mixture of paraffins and olefins (for example, a product stream from a steam naphtha cracker or a FCC process) using a high silicon content SAPO-11 catalyst with AEL structure. Preferred operating temperatures in the range 500° C. to 600° C. are indicated. The SAPO catalyst is shown by example to have higher activity and selectivity for propylene than conventional FCC catalyst additives such as ZSM-5. U.S. Pat. No. 6,300,537 and U.S. Pat. No. 6,521,563, both to Strohmaier et al. (and both assigned to ExxonMobil) show similar results using a different preparation of high silicon SAPO-11 designated ECR-42.

U.S. Pat. No. 6,258,257 to Swan et al. teaches a two stage process for producing C2 to C4 olefins from gas oil in which the gas oil is first contacted with an FCC catalyst to produce an olefinic naphtha stream and this naphtha stream is then contacted with ZSM-5 or other small or medium pore zeolites at a temperature in the range 630° C. to 650° C.

U.S. Pat. No. 6,791,002 to Abrevaya et al. teaches use of a plurality of riser reactors attached to a common regenerator, allowing each riser reactor to contact an oil stream at different conditions of temperature and residence time. Unconverted intermediate products from catalytic cracking of naphtha are recycled to different riser reactors where they are contacted with catalyst under the appropriate reaction conditions.

With the increasing demand for light olefins, improvements that can increase the yields without significantly increasing the capital expense or increasing the utility costs are important. Improvements and integration with other processes can improve yields of light olefins by increasing the utilization of other process streams. Also, improving the use of processes that yield intermediate process streams which can be diverted for conversion to light olefins can result in significant yield increases.

SUMMARY OF THE INVENTION

The present invention is a process for improving the light olefin yields associated with fluidized catalytic cracking. The fluidized catalytic cracking (FCC) process is used to convert larger hydrocarbons that are typically above the naphtha boiling range to light olefins. However, there are significant amounts of by-products that are passed to other processing units. The light olefin yields can be increased by adding small units to process some of the by-products, while utilizing the equipment associated with the FCC process for product recovery and heat exchange. The process includes separating the effluent stream from an FCC unit to create a first process stream having light olefins and a second process stream having olefins and paraffins in the C4 to C12 range. The second process stream is passed to an olefin conversion reactor to generate ethylene and propylene from the C4 to C12 process stream. The light olefins are separated and an olefin depleted stream is generated. The olefin depleted stream has a relative increased paraffinic content, and is passed to a dehydrogenation reactor to generate a third process stream with an increased olefin content. The third process stream is then passed to the olefin conversion reactor.

In one embodiment, the olefin conversion reactor is an olefin cracking reactor to convert the larger olefins to light olefins. The process can also use a first olefin conversion reactor that is either an olefin cracking reactor, alkylation reactor, or an etherification reactor, and a second olefin conversion reactor which can be the same as the first olefin conversion reactor or different type of reactor from those listed above for the conversion of olefins.

Additional objects, embodiments and details of this invention can be obtained from the following detailed description of the invention.

DETAILED DESCRIPTION OF THE INVENTION

In hydrocarbon processing, and in particular fluidized catalytic cracking (FCC), a significant amount of light paraffins in the C4 to C6 range are generated. These paraffins have low economic value and are not highly desirable for use in fuels. It is preferred to convert these to higher value products, but with the low reactivity of paraffins, this is not easily accomplished. The present invention takes these low value hydrocarbons and upgrades them for conversion to more valuable products, such as olefins and aromatics. The low value hydrocarbons include unreacted, or uncracked, paraffins and naphthenes in the gasoline range cut. The addition of small units that can convert these low value hydrocarbons can take advantage of the energy and process streams already generated by the fluidized catalytic cracking process.

The FCC process cracks a heavier hydrocarbon stream, such as a vacuum gas oil stream, and produces a light olefin product comprising ethylene and propylene. The FCC process also produces significant amounts of other hydrocarbons that are not converted to ethylene or propylene. In the FCC process, the catalyst used can be enhanced with a second catalyst, such as ZSM-5. The second catalyst is added to crack larger paraffins. However, the cracking requires pushing the operation limits, such as increasing the temperature, to increase the light olefin output. This presents other problems, such as shortening the life of the catalyst, and shortening the cycle time for passing catalyst between the reactor and regenerator. Lighter paraffins in the C4 to C6 range are also generated. The paraffins can be upgraded to more reactive materials through conversion to olefins. The olefins can then be processed in other reactors, or recycled back to the catalytic cracking reactor to further increase the light olefin yield.

Historically, the primary issues limiting this potential route are the high cost of small scale units and the low margins on the upgraded products, or for conversion of products for applications that convert one material to another. The present invention aims to take advantage by integrating small units that further enhances light olefin production and can use the existing product recovery and catalyst regeneration system. This produces a cost effective method of enhancing light olefin production in a commercial catalytic cracking process.

The present invention adds small scale dehydrogenation units to the FCC process to convert uncracked paraffins to olefins. The units are integrated into a light olefin production process to increase the amount of olefins through dehydrogenation of unreacted paraffins from an FCC unit. The present invention comprises converting a hydrocarbon stream to light olefins. The hydrocarbon stream is passed to a fluid catalytic cracking reactor where a cracked effluent stream is created comprising olefins and paraffins. The effluent stream is separated into a first process stream comprising light olefins and paraffins and other hydrocarbons, and a second process stream comprising olefins and heavier paraffins. The heavier paraffins have 4 or more carbons and will generally be in the C4 to C12 range. The second stream is passed to an olefin conversion reactor, where an olefin conversion effluent stream having increased light olefins is generated. The olefin conversion effluent stream is separated into an olefin product stream and an olefin depleted stream. The olefin depleted stream comprises paraffins and naphthenes, and is passed to a dehydrogenation reactor to create an effluent stream having an increased level of olefins and aromatics. The dehydrogenation reactor generates a third stream having an increased olefin content. The third stream can be passed back to the olefin conversion reactor to increase the amount of light olefins. This process can be repeated until the majority of the naphtha range paraffins present in the FCC unit effluent have been converted to other products. One type of olefin conversion reactor is an olefin cracking reactor, wherein heavier olefins, such as butenes, also known as butylenes, and pentenes are cracked to produce ethylene and propylene. For a process stream relatively rich in olefins in the C4 to C12 range, olefin cracking is desirable, with the recycling of any C4 or greater olefin components in the product stream.

In controlling the product stream, when it is desirable to increase the propylene product, a portion of the ethylene stream can also be recycled to one of the olefin conversion reactors, such as the alkylation reactor to increase the size of the olefins before the alkylation effluent stream to the olefin cracking reactor. In one embodiment, the second conversion reactor can be an alkylation reactor. The alkylation reactor can react butenes with butanes and other residual alkanes or alkenes to produce larger olefins or paraffins, as well as ethylene with larger hydrocarbons to produce larger olefins or paraffins. The larger olefins and paraffins can be recycled to an olefin cracking reactor and optionally a dehydrogenation reactor to increase the amounts of ethylene and propylene or the heavier olefins or paraffins can be recovered as a desirable product. Reaction conditions in an alkylation reactor include temperatures between 40° C. and about 120° C., pressures between 350 kPa (50 psia) and 1.4 MPa (200 psia), and a weight hourly space velocity (WHSV) between 0.1 hr$^{-1}$ and 30 hr$^{-1}$. Preferably, the WHSV is between 1 hr$^{-1}$ and 10 hr$^{-1}$.

The effluent streams comprising ethylene and propylene from the additional reactors can be cycled through the same equipment for recovering light olefins from the FCC process.

Olefin cracking reactors can be fixed bed reactors, fluidized bed reactors, or a continuous catalyst regeneration (CCR) system. For fixed bed reactors, a plurality of reactors are used with one reactor on-line, while subsequent reactors are regenerated off-line. The fixed reactor beds are switched when the catalyst in the on-line reactor bed is sufficiently deactivated that regeneration is required. Fluidized bed reactors can be operated as continuous reaction-regeneration systems with the catalyst cycled between the reactor and regenerator. These reactor types are known and specific design details are determined based on the quality and quantity of reactor streams processed. The olefin reaction cracking conditions include a temperature between 500° C. to 650° C., and preferable between 550° C. to 620° C. The olefin cracking conditions are operated at relatively low pressures between 100 kPa (14.5 psia) and 400 kPa (58 psia), and preferably between 120 kPa (17.4 psia) and 250 kPa (36.3 psia). The weight hourly space velocity (WHSV) for the olefin cracking unit is between 5 and 40 hr$^{-1}$.

In one embodiment, the catalyst in the olefin conversion reactor uses the same catalyst as used in the fluid catalytic cracking unit. Using the same catalyst allows for passing the catalyst to the same regeneration reactor, and does not require the addition of a separate regeneration reactor for the olefin conversion reactor.

In another embodiment, the process further comprises separating the effluent stream from the dehydrogenation reactor into a fourth stream having C5 and heavier hydrocarbons, and a fifth stream having butanes and butenes. The C5 and heavier hydrocarbons, comprising heavier olefins is passed to the olefin cracking reactor to increase the light olefins. The butanes and butenes stream is passed to a second olefin conversion reactor. The second olefin conversion reactor can be an alkylation reactor to generate larger olefin constituents, which can be passed to the olefin cracking reactor or the alkylation reactor can generate heavier paraffins that can be recovered as a hydrocarbon product. Optionally, the second conversion reactor can be an etherification reactor where the heavier olefins are olefins are reacted with methanol to create ether compounds. The ether compounds are then processed in a separate reactor to convert the ethers to an effluent stream having light olefins. The effluent stream is then processed through the existing separation equipment to recover the light olefins. Another option is to pass an ethylene rich stream and the fifth stream comprising butanes and butenes to a metathesis reactor. The ethers can also be recovered as a separate product.

The dehydrogenation reactors in the present invention are small scale units, and can comprise fixed bed reactors or fluidized bed reactors. With fixed bed reactors at least two reactors are used where one reactor is on-line and the other reactors are off-line to be regenerated. The size and number of reactors is chosen based upon the cycle times for operation of the reactor on-line, and the amount of time required to regenerate the reactor when the reactor is off-line. The fluidized bed reactor can be operated continuously in a reactor-regenerator system where the catalyst cycles through the reactor and regenerator.

When fixed bed reactors are used, the process is intended to be rapid with a relatively short cycle time. The cycle time between process and regeneration is expected to be between 10 to 20 minutes. During regenerations, coke is burned off and the catalyst is heated up, with most of the energy for burning the coke supplied by an external gas fired heater. The heat can also be supplied directly from the FCC regenerator flue gas, or through heat exchange with the regenerator flue gas. After regeneration, the heated catalyst provides most or all of the necessary heat of reaction for the dehydrogenation process. The dehydrogenation reactors have typically a low pressure drop, so the regeneration air can be once-through, and then returned to the FCC flue gas system, which eliminates the need for a small scale regeneration air system. The air required for regeneration is most preferably supplied either directly from the FCC regenerator main air blower or from the FCC regenerator flue gas.

The dehydrogenation step includes contacting hydrocarbon feeds rich in paraffins with a catalyst to convert the paraffins to olefins. The catalyst used in a dehydrogenation reactor includes metals on a support. Preferable metals include platinum (Pt), chromium (Cr), zirconium (Zr), and a zirconium-chromium blend. When the metal is zirconium, chromium, or a zirconium-chromium blend, the catalyst can be just the metal without a support. Dehydrogenation catalysts can also include mixtures of the metals. Supports include molecular sieves, zeolites, carbon, metal oxides, and mixtures thereof.

Dehydrogenation conditions include a temperature of generally from about 400° C. (752° F.) to about 900° C. (1652° F.) and preferably from about 420° C. (788° F.) to about 600° C. (1112° F.), a pressure of generally from about 1 kPa(g) (0.15 psi(g)) to about 1000 kPa(g) (145 psi(g)), and a LHSV of from about 0.1 to about 100 hr$^{-1}$. As used herein, the abbreviation "LHSV" means liquid hourly space velocity, which is defined as the volumetric flow rate of liquid per hour divided by the catalyst volume, where the liquid volume and the catalyst volume are in the same volumetric units. Generally for normal paraffins, the lower the molecular weight the higher the temperature required for comparable conversion. The pressure in the dehydrogenation zone is maintained as low as practicable, usually less than 350 kPa(g) (50.8 psi(g)) to maximize chemical equilibrium advantages.

The combination of the FCC and this invention produce a mix of hydrocarbon components in the process streams. The effluent streams from the dehydrogenation reactor are subsequently cooled and compressed to facilitate separation into individual product streams. Dehydrogenation reactor effluent streams can be cooled using various heat exchange methods such as, for example, indirect heat exchange with a cooling medium such as, for example, cooling water. One such indirect heat exchange method generally involves passing the hot dehydrogenation reactor effluent stream through a heat exchange unit such as, for example, a tube and sheet heat exchanger, to produce a cooled effluent stream having a temperature profile that is suitable for efficient compression. These heat exchange steps can be incorporated into existing equipment already associated with the FCC process. This provides an increase in product yield while minimizing additional equipment and energy costs.

In another embodiment, the separation of FCC product streams can include the separation of aromatic compounds from the olefin depleted streams before further processing. The olefin depleted streams after removal of the aromatic compounds are then passed to the dehydrogenation reactor, where the paraffinic compounds are converted to olefins and naphthenic compounds will be converted to additional aromatics.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for converting a hydrocarbon stream to light olefins, comprising:
    passing a hydrocarbon stream to a fluid catalytic cracking (FCC) unit, thereby creating a cracked effluent stream;
    separating the cracked effluent stream, thereby creating a first process stream comprising light olefins, and a second process stream comprising olefins and paraffins in the C4 to C12 range;
    passing the second stream to an olefin cracking reactor, thereby creating a conversion product stream with an increased content of light olefins;
    separating the conversion product stream into a light olefin product stream, and a light olefin depleted stream comprising paraffins and naphthenes;
    passing the light olefin depleted stream to a dehydrogenation reactor, thereby creating a third process stream with an increased level of olefins, wherein:
    the dehydrogenation reactor is part of a dehydrogenation reactor/regenerator system, the dehydrogenation reactor/regenerator system uses a short cycle time between 10 and 20 minutes, the regenerator provides heat for the dehydrogenation reactor, an FCC regenerator flue gas supplies heat to the regenerator, and the dehydrogenation reactor includes a catalyst comprising a metal on a support, wherein the metal is selected from the group consisting of Pt, Cr, Zr, a Zr—Cr blend, and mixtures thereof; and
    passing the third process stream to an olefin conversion reactor; wherein light olefins comprise ethylene and propylene.

2. The process of claim 1 wherein the olefin cracking reactor is a fixed bed reactor.

3. The process of claim 1 wherein the olefin cracking reactor uses a continuous catalyst regeneration system.

4. The process of claim 1 wherein the olefin cracking reactor is a fluidized bed reactor.

5. The process of claim 1 wherein the dehydrogenation reactor is at least two fixed bed reactors.

6. The process of claim 1 wherein the dehydrogenation reactor is a fluidized bed reactor.

7. The process of claim 1 further comprising recovering propylene from the light olefin product stream, thereby creating a propylene stream.

8. The process of claim 1 further comprising recovering ethylene from the olefin product stream, thereby creating an ethylene stream.

9. The process of claim 1 further comprising separating aromatic compounds from the light olefin depleted stream before passing the light olefin depleted stream to the dehydrogenation reactor.

10. A process for converting a hydrocarbon stream to light olefins, comprising:
    passing a hydrocarbon stream to a fluid catalytic cracking (FCC) unit having an FCC reactor and FCC catalyst regenerator, thereby creating a cracked effluent stream;
    separating the cracked effluent stream, thereby creating a first process stream comprising light olefins, and a second process stream comprising olefins and paraffins in the C4 to C12 range;
    passing the second stream to an olefin cracking reactor, thereby creating a conversion product stream comprising light olefins;
    separating the conversion product stream into a light olefin product stream, and a light olefin depleted stream comprising paraffins and naphthenes;
    passing the light olefin depleted stream to a dehydrogenation reactor, thereby creating a third process stream having an increased content of olefins, wherein:
    the dehydrogenation reactor is part of a dehydrogenation reactor/regenerator system, the dehydrogenation reactor/regenerator system uses a short cycle time between 10 and 20 minutes, the FCC catalyst regenerator supplies heat for the dehydrogenation regenerator, the dehydrogenation regenerator provides heat for the dehydrogenation reactor, and the dehydrogenation reactor includes a catalyst comprising a metal on a support, wherein the metal is selected from the group consisting of Pt, Cr, Zr, a Zr—Cr blend, and mixtures thereof;
    separating the third process stream into a fourth process stream comprising C5+ hydrocarbons, and a fifth process stream comprising butanes and butenes;
    passing the fourth process stream to the olefin cracking reactor and
    passing the fifth process stream to a conversion reactor; wherein light olefins comprise ethylene and propylene.

11. The process of claim 10 wherein the conversion reactor is an alkylation reactor.

12. The process of claim 10 wherein the conversion reactor is a metathesis reactor and ethylene is passed with the fifth process stream to the metathesis reactor.

* * * * *